US010793766B2

(12) United States Patent
Vanzin et al.

(10) Patent No.: US 10,793,766 B2
(45) Date of Patent: Oct. 6, 2020

(54) SULFOSUCCINATE SURFACTANT COMPOSITIONS AND METHODS USING THE SAME

(71) Applicant: Cytec Industries Inc., Princeton, NJ (US)

(72) Inventors: David Vanzin, Franklin, TN (US); Shailesh Majmudar, Stamford, CT (US); Nimal Jayasuriya, Shelton, CT (US); Azhar M. Awan, Woodstock, GA (US)

(73) Assignee: Cytec Industries Inc., Princeton, NJ (US)

( * ) Notice: Subject to any disclaimer, the term of this patent is extended or adjusted under 35 U.S.C. 154(b) by 0 days.

(21) Appl. No.: 15/436,021

(22) Filed: Feb. 17, 2017

(65) Prior Publication Data

US 2018/0051201 A1 Feb. 22, 2018

Related U.S. Application Data

(60) Provisional application No. 62/376,674, filed on Aug. 18, 2016.

(51) Int. Cl.
| | |
|---|---|
| *C09K 8/584* | (2006.01) |
| *C07C 309/17* | (2006.01) |
| *C09K 8/68* | (2006.01) |
| *C09K 8/60* | (2006.01) |
| *C11D 1/37* | (2006.01) |
| *C09K 8/62* | (2006.01) |
| *E21B 43/116* | (2006.01) |
| *C11D 1/12* | (2006.01) |
| *E21B 43/26* | (2006.01) |

(52) U.S. Cl.
CPC ............ *C09K 8/584* (2013.01); *C07C 309/17* (2013.01); *C09K 8/602* (2013.01); *C09K 8/62* (2013.01); *C09K 8/68* (2013.01); *C11D 1/37* (2013.01); *E21B 43/116* (2013.01); *C11D 1/123* (2013.01); *E21B 43/26* (2013.01)

(58) Field of Classification Search
CPC .......... C09K 8/584; C09K 8/68; C09K 8/035; C09K 8/40; C09K 8/467; C09K 8/487; C09K 8/602; C09K 8/725; C09K 8/88; C09K 2208/12; C09K 2208/26; C09K 2208/32; C09K 3/1409; C09K 3/1436; C09K 3/1463; C09K 8/12; C09K 8/594; C09K 8/62; C09K 8/665; C09K 8/74; C09K 8/80; C09K 8/86; C09K 8/882; C09K 8/94; E21B 43/16; E21B 43/26; E21B 21/003; E21B 33/138; E21B 43/267
See application file for complete search history.

(56) References Cited

U.S. PATENT DOCUMENTS

| | | | |
|---|---|---|---|
| 2,028,091 A | 1/1936 | Jaeger | |
| 2,658,036 A * | 11/1953 | Core | C23F 11/188 507/256 |
| 3,301,328 A * | 1/1967 | Campion | C09K 8/584 166/305.1 |
| 3,333,364 A | 8/1967 | Herr | |
| 3,333,634 A | 8/1967 | Townsend et al. | |
| 3,793,218 A | 2/1974 | Canevari | |
| 3,811,504 A | 5/1974 | Flournoy et al. | |
| 3,827,497 A | 8/1974 | Dycus et al. | |
| 3,890,239 A | 6/1975 | Dycus et al. | |
| 3,947,400 A | 3/1976 | Burkhard et al. | |
| 4,018,689 A | 4/1977 | Thompson | |
| 4,196,092 A | 4/1980 | Wang et al. | |
| 4,252,657 A | 2/1981 | Barriol et al. | |
| 4,271,907 A | 6/1981 | Gale | |
| 4,434,087 A | 2/1984 | Hampson et al. | |
| 4,825,950 A | 5/1989 | Kalpakci et al. | |
| 5,609,998 A * | 3/1997 | Texter | G03C 1/005 430/449 |
| 7,373,977 B1 | 5/2008 | Berger et al. | |
| 7,482,310 B1 | 1/2009 | Reese et al. | |
| 7,566,098 B2 | 7/2009 | Na | |
| 2005/0067194 A1 | 3/2005 | Pena et al. | |
| 2006/0260815 A1 | 11/2006 | Dahanayake et al. | |
| 2007/0116524 A1 | 5/2007 | Shiau | |
| 2008/0200565 A1 | 8/2008 | Harwell et al. | |
| 2008/0302531 A1 | 12/2008 | Berger et al. | |
| 2011/0174485 A1 | 7/2011 | Robb et al. | |
| 2013/0267570 A1 * | 10/2013 | Premachandran | A01N 43/16 514/372 |
| 2014/0135239 A1 * | 5/2014 | Fellows | C09K 8/54 507/255 |

(Continued)

FOREIGN PATENT DOCUMENTS

| | | | |
|---|---|---|---|
| CA | 2777535 A1 | 4/2011 | |
| CN | 103320103 A | 9/2013 | |
| CN | 103803764 | * 5/2014 | |

(Continued)

OTHER PUBLICATIONS

Scifinder document downloaded on Jul. 19, 2018.*
International Search Report and Written Opinion issued in corresponding PCT Application No. PCT/US2017/018349, dated Jun. 6, 2017, pp. 1-14.
Kmetz, Anthony A., et al., Improved Mobility of Magnetite Nanoparticles at High Salinity with Polymers and Surfactants, Enerygy & Fuels, 2016, pp. 1915-1926, vol. 30(3), American Chemical Society, USA.

(Continued)

*Primary Examiner* — Kumar R Bhushan
(74) *Attorney, Agent, or Firm* — Charles E. Bell, Esq.; Robert Kasten; Elizabeth Galetta, Esq.

(57) ABSTRACT

Sulfosuccinate surfactant compounds blended in binary and ternary combinations to yield synergistic sulfosuccinate surfactant systems and use of the same in enhanced oil recovery and hydraulic fracturing applications.

9 Claims, No Drawings

(56) References Cited

U.S. PATENT DOCUMENTS

2014/0262286 A1  9/2014  Dwarakanath et al.
2017/0051195 A1  2/2017  Vanzin et al.

FOREIGN PATENT DOCUMENTS

| DE | 2525996 A1 | 12/1976 |
|---|---|---|
| EP | 2268764 B1 | 3/2014 |
| GB | 1524448 | 9/1978 |
| WO | 2006108161 A2 | 10/2006 |
| WO | 2013184116 A1 | 12/2013 |
| WO | 2016196413 A1 | 12/2016 |

OTHER PUBLICATIONS

Office Action of U.S. Appl. No. 15/240,573, dated Nov. 2, 2017, pp. 1-7.
Office Action of U.S. Appl. No. 15/168,220, dated Mar. 22, 2019, pp. 1-9.

* cited by examiner

SULFOSUCCINATE SURFACTANT COMPOSITIONS AND METHODS USING THE SAME

CROSS REFERENCE TO RELATED APPLICATIONS

The instant application is a non-provisional patent application of, and claims priority benefit to, U.S. Provisional Application No. 62/376,674, entitled "Sulfosuccinate Surfactant Compositions and Methods Using the Same," filed on Aug. 18, 2016, which is hereby incorporated by reference in its entirety.

FIELD OF THE INVENTION

This invention relates to surfactant systems that achieve both low surface tension and low interfacial tension for usage in oil field applications, specifically enhanced oil recovery and fracking. Other applications for the surfactant systems disclosed herein include, but are not limited to, applications within the oil and other industries (i.e. drilling muds, oil field dispersants, oil field wetting agents, paints/coatings, adhesives, overprint varnishes, building/construction, metalworking fluids, surface cleaners, polymers).

BACKGROUND

Crude oil is typically recovered from oil bearing reservoirs by three processes, generally categorized as primary, secondary or tertiary recovery. In primary recovery, the oil is produced through a producing well by taking advantage of the pressure exerted by underground pools of water and gas or by water present in the oil. Approximately 20% of the original oil in place (OOIP) is recovered by this process. Once this pressure has been exhausted, other means of recovery of the remaining oil must be employed.

In secondary recovery, the well may be re-pressurized with gas or water injected through one of the injection wells to recover an additional 20% of the OOIP. Other secondary recovery methods include, for example, acidizing and/or fracturing to create multiple channels through which the oil may flow.

After secondary recovery means have been exhausted and are failing to produce any additional oil, tertiary recovery can be employed to recover additional oil up to approximately 60% of the OOIP. Tertiary recovery processes include, but are not limited to, steam flooding, polymer flooding, microbial flooding and chemical flooding.

Within the oil containing reservoir, there are a number of factors that can influence the amount of oil recovered. Many of these factors are related to the water utilized in the flood and its interaction with the oil and the rock surfaces within the reservoir formation. It is often common practice to incorporate surfactants into the secondary and tertiary recovery processes to assist in lowering the surface tension of the water to more effectively wet the formation and to lower the interfacial tension between the water and the oil in order to more effectively release the oil. The ability of the water to possess lower surface tension is a desired effect as it allows the water to come into intimate contact with the rocks in the formation, essentially modifying their wettability and easing and improving the release and extraction of the oil by lowering the surface tension of aqueous liquids, solid matter can be more easily wet out by the liquid. This property is useful when treating subterranean formations with various aqueous liquids to stimulate the flow of petroleum and/or aqueous fluids therefrom.

Low surface tension, in combination with the water wetting properties of an aqueous liquid, reduces the capillary forces in the formation that is being treated. Reduction in the capillary forces in a reservoir results in a more effective recovery of fluids after the formation has been treated. It is well known that lowering the interfacial tension between the water and the oil is a greatly desired effect as this lower interfacial tension allows for the water and oil to come into intimate contact and for the oil to be released into the water flood stream and flow to the production well where it can be recovered.

In many enhanced oil recovery operations, the source of the water is brine. Brine is an aqueous solution of salts and may contain various metal ions such as sodium, calcium, magnesium, potassium, barium, zinc, and others and anions such as chloride, sulfate, carbonate, bicarbonate, and others. The use of surfactants to reduce the surface and interfacial tension between the water and the oil to be displaced from the formation is well known, and the literature is replete with different surfactants and combinations thereof useful in water flooding processes. It is well known that the effectiveness of any given surfactant material varies considerably with such factors as temperature of the water, the amount of salt in the water, the amount and type of metal ions in the water and the like. Additionally, the rock formation itself, e.g. limestone or sandstone, can influence surfactant selection and performance as well as the nature and type of the oil being extracted. Precipitation of surfactant leads to a loss in the efficiency of recovery as the surfactant no longer can serve to wet the formation and lower interfacial tension. Additionally, the surfactant can plug channels within the formation, decreasing formation porosity and injectivity, thereby causing a substantial decrease in oil displacement efficiency.

These oil recovery techniques typically employ significant quantities of water in combinations with steam, polymers, microbes and chemicals. In secondary and tertiary recovery, the fluid is injected into one or more injection wells and passes into the formation. Oil is then displaced within the formation and moves through the formation and is produced at one or more production wells.

Secondary and tertiary oil recovery is enhanced through the incorporation of surfactants that assist in improving the microscopic displacement of oil within the subterranean formation. The surfactants increase and improve the miscibility of the water and the oil in the formation, assisting in its release and recovery. This is because the surfactant lowers the interfacial tension between the water and the oil and in some cases the unfavourable contact angle made by the interface of the two liquids and the solid surface. As a result, the water is able to penetrate the microspores and other smaller pores in the formation and improve the recovery of the oil. Thus, the microscopic sweep efficiency of the tertiary fluid is enhanced, as the percentage ratio of the amount of oil displaced out of the pore space of the portion of the formation through which the flooding liquid has passed to the original amount of oil therein.

The current art details the usage of many types of surfactants to lower either surface or interfacial tension in enhanced oil recovery and fracking operations. Some of the types of surfactants detailed in the art as generating low surface and interfacial tension include anionics, cationics, amphoterics and nonionics. Specific chemical classes would include alkyl sulfonates, alkyl aryl sulfonates, alkyl diphenyl ether disulfonates, aryl sulfonates, alphaolefin sulfonates, petroleum sulfonates, alkyl sulfates, alkylether sulfates, alkylarylether sulfates, ethoxylated and propoxylated alcohols, fluorosurfactants, sorbitan and ethoxylated sorbitan esters, glucose esters, polyglucosides, phosphate esters, amine oxides, alkyl amido betaines, imidazolines. sulfosuccinates and blends of these materials.

In the selection of surfactants for enhanced oil recovery applications, the oil and conditions of the reservoir can greatly influence surfactant selection and performance. In selecting surfactants that will serve to lower both surface and interfacial tension, one must examine the performance of the surfactants in formulations and environments that will approximate the end use application. Selection of a surfactant to lower surface and interfacial tension is influenced by surfactant chemistry, brine composition, nature of the porous media, temperature and pressure. Ideally, one is looking for a surfactant system that exhibits good solubility in the brine at surface and reservoir conditions, has appropriate thermal stability under reservoir conditions and has a low adsorption onto the reservoir rock.

Some of the weaknesses of surfactants covered by the prior art include (1) may be good for reducing surface tension (i.e. wetting) or lowering interfacial tension (improving oil release/recovery) but not offering both properties in the same formulation; (2) functionality limited to specific types of oils and reservoirs; (3) effective concentration ranges of the surfactant is too narrow; (4) high temperature stability and functionality; (5) the surfactant is not readily dispersible or soluble in the formation brine; (6) the flash point of the surfactant is low, creating hazards and additional expenses for transfer, storage, mixing and special handling; (7) high surfactant adsorption onto the formation; and (8) the surfactant is manufactured from materials that are in short supply and not readily available for full scale manufacture.

While the prior art does include references to using sulfosuccinates in combination with other anionic, cationic and non-ionic surfactants in secondary (hydraulic fracturing) and tertiary oil recovery, their usage has been limited due to product solubility, stability, functionality and handling. Specifically, with respect to sulfosuccinate product functionality, the ability of the products to perform in varying reservoirs and lower both surface and interfacial tension, with various types of oil, a range of brine concentrations and over a range of temperatures has been limited.

Thus, there exists a need in the market for a surfactant system that could be broadly applicable to both secondary (i.e. hydraulic fracturing and water flooding) and tertiary oil recovery. Such a surfactant system would offer both low surface tension, which would facilitate its ready wetting out of the rock formation (also referred to herein as a "subterranean formation" or "formation"), and low, to ultra-low, interfacial tension allowing it to more easily release oil entrapped within the rock. It would also be highly advantageous if the surfactants systems were safe and easy to handle.

SUMMARY OF THE INVENTION

This invention and the instant disclosure is directed to sulfosuccinate surfactants combinations yield synergistic surfactant systems that offer low surface tension and/or low interfacial tension. The surfactant systems are also functional over a broad range of temperature and salinity and select products evidenced increased solubility and compatibility in a variety of brine salinities.

In one embodiment, the surfactant systems disclosed herein are broadly applicable to oil recovery including both secondary (i.e. hydraulic fracturing and water flooding) and tertiary oil recovery. In one embodiment, the surfactant systems disclosed herein offer both low surface tension, which would facilitate its ready wetting out of the rock formation, and low, to ultra-low, interfacial tension allowing it to more easily release oil entrapped within the subterranean formation.

The surfactant systems disclosed herein are safe and easy to handle.

One embodiment is directed to a surfactant system comprising: a mixture of:

(a) one or more of a first diester sulfosuccinate surfactant compound according to formula (I):

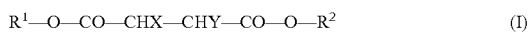
$$R^1-O-CO-CHX-CHY-CO-O-R^2 \qquad (I)$$

wherein:
$R^1$ and $R^2$ are linear or branched alkyl groups, each independently having from eight to thirteen carbon atoms (C8-C13),
X is —H or —SO$_3^-$M$^+$, and
Y is —H or —SO$_3^-$M$^+$,
when X is —H, then Y is —SO$_3^-$M$^+$ and when Y is —H, then X is —SO$_3^-$M$^+$, where M$^+$ is H$^+$, Na$^+$, K$^+$, Ca$^{2+}$, Mg$^{2+}$, NH$_4^+$, NR$_4^+$, where R is H, methyl, ethyl, propyl or butyl; and (b) one or more of a second diester sulfosuccinate surfactant compound according to formula (II):

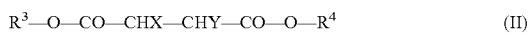
$$R^3-O-CO-CHX-CHY-CO-O-R^4 \qquad (II)$$

wherein:
$R^3$ and $R^4$ are linear or branched alkyl groups, each independently having from four to seven carbon atoms (C4-C7),
X is as defined according to formula (I), and
Y is as defined according to formula (I),
wherein if $R^1$ and $R^2$ are C8, then $R^3$ and $R^4$ are C4, C5 or C7, and
wherein, if $R^3$ and $R^4$ are C6, then $R^1$ and $R^2$ are C9-C13.

Another embodiment is directed to a surfactant system comprising:
a mixture of:

(a) one or more of a first diester sulfosuccinate surfactant compound according to formula (I):

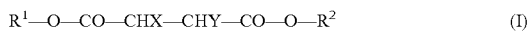
$$R^1-O-CO-CHX-CHY-CO-O-R^2 \qquad (I)$$

wherein:
$R^1$ and $R^2$ are linear or branched alkyl groups, each independently having from eight to thirteen carbon atoms,
X is —H or —SO$_3^-$M$^+$, and
Y is —H or —SO$_3^-$M$^+$.
when X is —H, then Y is —SO$_3^-$M$^+$ and when Y is —H, then X is —SO$_3^-$M$^+$, where M$^+$ is H$^+$, Na$^+$, Ca$^+$, Mg$^+$, K$^+$, NH$_4^+$, NR$_4^+$, where R is H, methyl, ethyl, propyl or butyl; and (b) one or more of a first monoester sulfosuccinate surfactant compound according to formula (III):

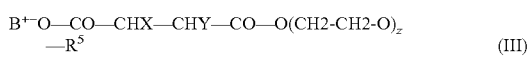
$$B^+-O-CO-CHX-CHY-CO-O(CH2-CH2-O)_z-R^5 \qquad (III)$$

wherein:
B$^+$ is Na$^+$, K$^+$, Ca$^+$, Mg$^+$, NH$_4^+$, or NR$_4^+$, where R is H, methyl, ethyl, propyl or butyl,
X is as defined for formula (I),
Y is as defined for formula (I), and
Z is 0-30, and $R^5$ is a linear or branched alkyl group having from eight to twenty carbon atoms (C8-C20).

Another embodiment is directed to a method of using one or more of the aforementioned surfactant systems in recovery of oil from a subterranean formation, the method comprising: combining an effective amount of one or more of the aforementioned surfactant systems with a brine to form a solution; injecting an effective amount of the solution into a subterranean formation; and increasing a pressure in the subterranean formation, thereby enabling the recovery of oil from the subterranean formation.

DETAILED DESCRIPTION

This invention is based on blends of sulfosuccinate surfactant compounds to form surfactant systems. One embodiment is directed to a surfactant system having a binary blend of two different diester sulfosuccinate surfactant compounds. Another embodiment is directed to a surfactant system having a binary blend of a diester sulfosuccinate surfactant compound and a monoester sulfosuccinate surfactant compound. A further embodiment is directed to a surfactant system having a ternary blend of two different diester sulfosuccinate surfactant compounds and a monoester sulfosuccinate surfactant compound.

The surfactant systems described herein are useful in many applications, including, but not limited to, oil field applications. Examples of oil field applications include, but are not limited to, Enhanced Oil Recovery (EOR) and Hydraulic Fracturing ("fracking"), and are generally referred to herein as "oil recovery" or "recovery of oil". Other applications include, for example, drilling muds, oil field dispersants, oil field wetting agents, paints/coatings, adhesives, overprint varnishes, building/construction, metalworking fluids, surface cleaners, polymers, and the like.

The surfactant system including a binary blend of two different diester sulfosuccinate compound includes a first diester sulfosuccinate compound and a second diester sulfosuccinate compound. The first diester sulfosuccinate surfactant compound is according to formula (I):

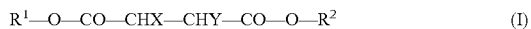

$$R^1\text{—}O\text{—}CO\text{—}CHX\text{—}CHY\text{—}CO\text{—}O\text{—}R^2 \quad (I)$$

wherein $R^1$ and $R^2$ are linear or branched alkyl groups, each independently having from eight to thirteen carbon atoms (C8-C13), X is —H or —SO$_3^-$M$^+$, and Y is —H or —SO$_3^-$M$^+$. when X is —H, then Y is —SO$_3^-$M$^+$ and when Y is —H, then X is —SO$_3^-$M$^+$, where M$^+$ is H$^+$, Na$^+$, K$^+$, Ca$^{2+}$, Mg$^{2+}$, NH$_4^+$, NR$_4^+$, where R is H, methyl, ethyl, propyl or butyl.

Examples of the first diester sulfosuccinate surfactant compound include, but are not limited to salts of di(n-octyl) sulfosuccinate, di(3-ethylhexyl) sulfosuccinate, di(isooctyl) sulfosuccinate, di(1-methylheptyl) sulfosuccinate, di(1-ethylhexyl) sulfosuccinate, di(2,4,4-trimethylpentyl) sulfosuccinate, di(n-nonyl) sulfosuccinate, di(2-ethylheptyl) sulfosuccinate, di(3,5,5-trimethylhexyl) sulfosuccinate, di(1-methyloctyl) sulfosuccinate, di(n-decyl) sulfosuccinate, di(2-propylheptyl) sulfosuccinate, di(3,7-dimethyloctyl) sulfosuccinate, di(n-undecyl) sulfosuccinate, di(n-dodecyl) sulfosuccinate, di(2-butyloctyl) sulfosuccinate, di(bistridecyl) sulfosuccinate and di(2-ethylhexyl) sulfosuccinate. In a particular embodiment, the first diester of the surfactant system is sodium bistridecyl sulfosuccinate or sodium di(2-ethylhexyl) sulfosuccinate.

The second diester sulfosuccinate surfactant compound of the surfactant system is according to formula (II):

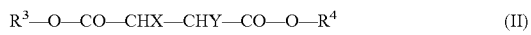

$$R^3\text{—}O\text{—}CO\text{—}CHX\text{—}CHY\text{—}CO\text{—}O\text{—}R^4 \quad (II)$$

wherein: $R^3$ and $R^4$ are linear or branched alkyl groups, each independently having from four to seven carbon atoms (C4-C7), X is as defined according to formula (I), and Y is as defined according to formula (I). In a particular embodiment, $R^3$ and $R^4$ are linear or branched alkyl groups, each independently having from four to six carbon atoms (C4-C6).

Examples of the second diester sulfosuccinate surfactant compound include, but are not limited to salts of di(n-butyl) sulfosuccinate, di(t-butyl) sulfosuccinate, di(1-methylpropyl) sulfosuccinate, di(n-pentyl) sulfosuccinate, di(1-methylbutyl) sulfosuccinate, di(2-methylbutyl) sulfosuccinate, di(isoamyl) sulfosuccinate, di(2,2-dimethylpropyl)) sulfosuccinate, di(n-hexyl) sulfosuccinate, di(2-ethylbutyl) sulfosuccinate, di(cyclohexyl) sulfosuccinate, di(3-methylpentyl) sulfosuccinate, di(1-methylpentyl) sulfosuccinate, di(n-heptyl) sulfosuccinate, di(5-methylhexyl) sulfosuccinate, di(1-methylhexyl) sulfosuccinate, di(2-ethylpentyl) sulfosuccinate, di (1,3-dimethylbutyl)sulfosuccinate, diamyl sulfosuccinate, and diisobutyl sulfosuccinate. In a particular embodiment, the second diester of the surfactant system is sodium di (1,3-dimethylbutyl) sulfosuccinate, sodium diamyl sulfosuccinate, or sodium diisobutyl sulfosuccinate.

In the binary surfactant system having two diester sulfosuccinate surfactant compounds, in the surfactant compound according to formula (I), if $R^1$ and $R^2$ are C8, then $R^3$ and $R^4$ in formula (II) are C4, C5 or C7. Thus, if the first diester sulfosuccinate surfactant is a salt of di(2-ethyl hexyl) sulfosuccinate, then the second diester sulfosuccinate surfactant is not a salt of di (1,3-dimethylbutyl) sulfosuccinate. In formula (II), if $R^3$ and $R^4$ are C6, then $R^1$ and $R^2$ in formula (I) are C9-C13. Thus, if the second diester sulfosuccinate surfactant is a salt of di (1,3-dimethylbutyl) sulfosuccinate, then the first diester sulfosuccinate surfactant is not a salt of di(2-ethylhexyl) sulfosuccinate.

A specific surfactant system having two diester sulfosuccinate surfactant compounds includes sodium bistridecyl sulfosuccinate as the first diester sulfosuccinate compound and sodium di (1,3-dimethylbutyl)sulfosuccinate, sodium diamyl sulfosuccinate, or sodium diisobutyl sulfosuccinate as the second diester sulfosuccinate compound. Another specific surfactant system having two diester sulfosuccinate surfactant compounds includes sodium di(2-ethyl hexyl) sulfosuccinate as the first diester sulfosuccinate compound and sodium diamyl sulfosuccinate or sodium diisobutyl sulfosuccinate as the second diester sulfosuccinate compound.

It is contemplated that the surfactant system having two different diester sulfosuccinate compound can include any amount of each diester sulfosuccinate compound. That is, both the first diester sulfosuccinate compound and the second diester sulfosuccinate compound can be present in a weight % ratio of from about 1 wt. % to about 99 wt. %, based on the total weight of the surfactant system. In a specific embodiment, the surfactant system includes the first diester sulfosuccinate surfactant is present in the surfactant system in a weight % ratio from 45 wt. % to 80 wt. % based on the total weight of the surfactant system, and the second diester sulfosuccinate surfactant is present in the surfactant system in a weight % ratio from 20 wt. % to 55 wt. % based on the total weight of the surfactant system.

Certain embodiments of the surfactant systems may include a mixture of the first diester sulfosuccinate surfactant compound according to formula (I) and a first monoester sulfosuccinate surfactant compound. The first monoester sulfosuccinate compound is according to formula (III):

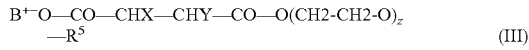
(III)

wherein: $B^+$ is $Na^+$, $K^+$, $Ca^+$, $Mg^+$, $NH_4^+$, or $NR_4^+$, where R is H, methyl, ethyl, propyl or butyl, X is as defined for formula (I), Y is as defined for formula (I), and Z is 0-30, and $R^5$ is a linear or branched alkyl group having from eight to twenty carbon atoms (C8-C20).

Formula (I) is described above. In one embodiment, $B^+$ is $Na^+$ in the first monoester sulfosuccinate surfactant compound and the first monoester sulfosuccinate surfactant compound is one of:

(a) disodium salt of poly(oxy-1,2-ethanediyl),α-(3-carboxy-1-oxosulfopropyl)-ω-hydroxy-C10-C16-alykyl ethers;

(b) disodium salts of butanedioic acid, 2-sulfo-,C9-11 isoalkyl esters, C10-rich; disodium salts of poly(oxy-1,2-ethanediyl),α-(3-carboxy-1-oxosulfopropyl)-ω-hydroxy-C12-14-alkyl ethers; and disodium salts of poly(oxy-1,2-ethanediyl),α-(3-carboxy-1-oxosulfopropyl)-ω-hydroxy-C10-12-alkyl ethers; and (c) sodium salt of poly(oxy-1,2-ethanediyl),α-(3-carboxy-1-oxosulfopropyl)-ω-(isotridecyloxy).

In a particular example, the surfactant system includes sodium bistridecyl sulfosuccinate as the first diester sulfosuccinate compound and one of:

(a) disodium salt of poly(oxy-1,2-ethanediyl),α-(3-carboxy-1-oxosulfopropyl)-ω-hydroxy-C10-C16-alykyl ethers;

(b) disodium salts of butanedioic acid, 2-sulfo-,C9-11 isoalkyl esters, C10-rich; disodium salts of poly(oxy-1,2-ethanediyl),α-(3-carboxy-1-oxosulfopropyl)-ω-hydroxy-C12-14-alkyl ethers; and disodium salts of poly(oxy-1,2-ethanediyl),α-(3-carboxy-1-oxosulfopropyl)-ω-hydroxy-C10-12-alkyl ethers; and (c) sodium salt of poly(oxy-1,2-ethanediyl),α-(3-carboxy-1-oxosulfopropyl)-ω-(isotridecyloxy). In another particular example, the surfactant system includes sodium di(2-ethyl hexyl) sulfosuccinate and one of (a), (b) and (c) of the first monoester sulfosuccinate compounds listed above.

It is contemplated that the surfactant system having the first diester sulfosuccinate compound and the first monoester sulfosuccinate compound can include any amount of each compound. That is, both the first diester sulfosuccinate compound and the first monoester sulfosuccinate compound can be present in a weight % ratio of from about 1 wt. % to about 99 wt. %, based on the total weight of the surfactant system. In one example, the first diester sulfosuccinate surfactant compound is present in the surfactant system in a weight % ratio from 45 wt. % to 80 wt. % based on the total weight of the surfactant system, and the first monoester sulfosuccinate surfactant compound is present in the surfactant system in a weight % ratio from 20 wt. % to 55 wt. % based on the total weight of the surfactant system.

A further embodiment of the surfactant system includes a ternary blend of a first diester sulfosuccinate surfactant compound according to formula (I), a second diester sulfosuccinate surfactant compound according to formula (II), and a first monoester sulfosuccinate surfactant compound according to formula (III). Formulae (I), (II) and (III), and the various examples thereof, are as described above. It is noted that in surfactant systems having a ternary blend of formulae (I), (II) and (III), when $R^1$ and $R^2$ of formula (I) is C8, then $R^3$ and $R^4$ of formula (II) can be C6, and when $R^3$ and $R^4$ of formula (II) are C6, $R^1$ and $R^2$ of formula (I) can be C8.

In one particular embodiment, the surfactant system having a ternary blend of compounds according to formulae (I), (II) and (III), the first diester sulfosuccinate surfactant compound is sodium di(2-ethyl hexyl) sulfosuccinate, the second diester sulfosuccinate surfactant compound is sodium di (1,3-dimethylbutyl)sulfosuccinate, and the first monoester sulfosuccinate surfactant compound is one of:

(a) disodium salt of poly(oxy-1,2-ethanediyl),α-(3-carboxy-1-oxosulfopropyl)-ω-hydroxy-C10-C16-alykyl ethers;

(b) disodium salts of butanedioic acid, 2-sulfo-,C9-11 isoalkyl esters, C10-rich; disodium salts of poly(oxy-1,2-ethanediyl),α-(3-carboxy-1-oxosulfopropyl)-ω-hydroxy-C12-14-alkyl ethers; and disodium salts of poly(oxy-1,2-ethanediyl),α-(3-carboxy-1-oxosulfopropyl)-ω-hydroxy-C10-12-alkyl ethers; and (c) sodium salt of poly(oxy-1,2-ethanediyl),α-(3-carboxy-1-oxosulfopropyl)-ω-(isotridecyloxy).

In a surfactant system having a ternary blend of sulfosuccinate surfactant compounds, i.e., a compound according to formulae (I), (II) and (III), the first diester sulfosuccinate surfactant compound is present in the surfactant system in a weight % ratio from 50 wt. % to 65 wt. % based on the total weight of the surfactant system, the second diester sulfosuccinate surfactant compound is present in the surfactant system in a weight % ratio from 20 wt. % to 30 wt. % based on the total weight of the surfactant system, and the first monoester sulfosuccinate surfactant compound is present in the surfactant system in a weight % ratio from 10 wt. % to 20 wt. % based on the total weight of the surfactant system. Surfactant systems were prepared by mixing together individual surfactants based on their solids content, at 50° C. for 1 hour.

The surfactant systems disclosed herein can be combined with other cationic, anionic, non-ionic and amphoteric surfactants, which can be added to the surfactant system at any amount needed or desired by the user. Examples of such additional surfactants include alkyl sulfonates, alkyl aryl sulfonates, alkyl diphenyl ether disulfonates, aryl sulfonates, alphaolefin sulfonates, petroleum sulfonates, alkyl sulfates, alkylether sulfates, alkylarylether sulfates, and fluoro surfactants.

The surfactant systems disclosed herein are suitable for use in low salinity (1-2%), medium salinity (3-6.5%) and high salinity (7 to 12%) range brines and are functional over a range of temperatures. Additionally, the disclosed surfactant systems can be optimized for a given set of oil field conditions. The disclosed surfactant systems can be used in hydraulic fracturing to aid in the wetting of the subterranean formation and the recovery of oil and gas. All of these surfactant formulations offer both low surface and interfacial tensions, performance at low concentrations and functionality over a range of salinities and temperatures.

The surfactant systems described herein are capable of being used as chemicals for releasing oil in enhanced oil recovery operations. The surfactant systems described herein are capable of being incorporated into an aqueous solution, such as water or brine, and then injecting, usually under high pressure, a solution of the sulfosuccinate system in brine to the subterranean formation via the injection well. The brine injected with the sulfosuccinate system can be a low salinity (1-2%), medium salinity (3-6.5%) or high salinity (7 to 12%) range brine, depending on the application and/or subterranean formation. Water based solutions of the sulfosuccinate surfactant system can be prepared by dissolving effective amounts of the surfactant compounds in propanol, isopropanol or a similar low molecular weight alcohol and thereafter adding the resultant alcoholic solution to water or brine in the desired concentration. Hydrocarbon solutions containing the sulfosuccinate surfactant system may be prepared by dissolving effective amounts the surfactant compounds in a highly aromatic oil or petroleum fraction. The effective amount in which the sulfosuccinate surfactant system is utilized in the oil or water based solution generally depends on the intended application, but is generally in a range between about 0.01 percent to about 5 percent by volume.

The quantity of the sulfosuccinate surfactant system containing solution ("solution") used will vary between applications. In general, the amount of solution utilized should range from about 50 to 250 gallons per foot of formation thickness. Greater or lesser quantities may be employed.

The solution is injected, with an oil pre-flush or after-flush optionally utilized, and the solution is allowed to stand for a period of time between about 1 hour to about 36 hours, however, other times are contemplated by the instant invention. Thereafter, the pressure is reduced and the solution and other fluids are pumped to the surface. This treatment can be repeated as necessary, thereby resulting in the recovery of oil.

The surfactant systems disclosed herein effectively lower surface tension and thus "wet out" the rock in the subterranean formation, thereby facilitating the flow of the aqueous solution through the reservoir. During this wetting process, the surfactant systems would come into intimate contact with the oil entrapped in the pores within the reservoir. The surfactant systems would effectively lower the interfacial tension between the water and the oil, allowing the entrapped oil to be released, flow through the reservoir and eventually recovered at the production well.

The surfactant systems disclosed herein are applicable to hydraulic fracturing, which is considered a secondary oil recovery technique. In this embodiment, the surfactant system, which makes up part of the chemical component of the injection fluid in the hydraulic fracturing application, lowers surface tension, aids in wetting out the rock formation, and lowers the interfacial tension between the oil and the water, increasing oil recovery and efficiency of the operation.

Other possible applications to which this invention could be applied would involve other processes where it is desired to achieve low surface and interfacial tension. Examples of envisioned applications include, for example, oil spill dispersant and oil field cleaning operations, drilling muds, oil sand treatment de-emulsifiers, dispersant to remove or prevent wax formation in pipelines, wetting agents for pipeline wells to reduce drag, wetting agents for acidizing formulations and soil remediation. Other applications to which this invention could be applied include wetting agents for coatings, adhesives, overprint varnishes, building and construction, paper and paperboard, nonwovens/textiles and polymers. One could also envision potential applications in agrochemicals, mining, pulp and paper, electronics and electrical and cleaning applications where it is advantageous to have low surface and/or low interfacial tension.

The present invention is further described in the following list of embodiments:

Embodiment 1

A surfactant system comprising:
a mixture of:
(a) one or more of a first diester sulfosuccinate surfactant compound according to formula (I):

$$R^1\text{—O—CO—CHX—CHY—CO—O—}R^2 \qquad (I)$$

wherein:
$R^1$ and $R^2$ are linear or branched alkyl groups, each independently having from eight to thirteen carbon atoms (C8-C13),
X is —H or —$SO_3^-M^+$, and
Y is —H or —$SO_3^-M^+$.
when X is —H, then Y is —$SO_3^-M^+$ and when Y is —H, then X is —$SO_3^-M^+$, where $M^+$ is $H^+$, $Na^+$, $K^+$, $Ca^{2+}$, $Mg^{2+}$, $NH_4^+$, $NR_4^+$, where R is H, methyl, ethyl, propyl or butyl; and
(b) one or more of a second diester sulfosuccinate surfactant compound according to formula (II):

$$R^3\text{—O—CO—CHX—CHY—CO—O—}R^4 \qquad (II)$$

wherein:
$R^3$ and $R^4$ are linear or branched alkyl groups, each independently having from four to seven carbon atoms (C4-C7),
X is as defined according to formula (I), and
Y is as defined according to formula (I),
wherein if $R^1$ and $R^2$ are C8, then $R^3$ and $R^4$ are C4, C5 or C7, and
wherein, if $R^3$ and $R^4$ are C6, then $R^1$ and $R^2$ are C9-C13.

Embodiment 2

The surfactant system according to embodiment 1, wherein $R^3$ and $R^4$ are linear or branched alkyl groups, each independently having from four to six carbon atoms (C4-C6).

Embodiment 3

The surfactant system according any one of the preceding embodiments, wherein the first diester sulfosuccinate surfactant compound according to formula (I) is a salt of di(n-octyl) sulfosuccinate, di(3-ethylhexyl) sulfosuccinate, di(isooctyl) sulfosuccinate, di(1-methylheptyl) sulfosuccinate, di(1-ethylhexyl) sulfosuccinate, di(2,4,4-trimethylpentyl) sulfosuccinate, di(n-nonyl) sulfosuccinate, di(2-ethylheptyl) sulfosuccinate, di(3,5,5-trimethylhexyl) sulfosuccinate, di(1-methyloctyl) sulfosuccinate, di(n-decyl) sulfosuccinate, di(2-propylheptyl) sulfosuccinate, di(3,7-dimethyloctyl) sulfosuccinate, di(n-undecyl) sulfosuccinate, di(n-dodecyl) sulfosuccinate, di(2-butyloctyl) sulfosuccinate, di(bistridecyl) sulfosuccinate, di(2-ethylhexyl) sulfosuccinate, or a combination thereof.

Embodiment 4

The surfactant system according to embodiment 3, wherein the first diester sulfosuccinate surfactant compound according to formula (I) is sodium bistridecyl sulfosuccinate, sodium di(2-ethyl hexyl) sulfosuccinate, or a combination thereof.

Embodiment 5

The surfactant system according to any one of the preceding embodiments, wherein the second diester sulfosuccinate surfactant compound according to formula (II) is a salt of di(n-butyl) sulfosuccinate, di(t-butyl) sulfosuccinate, di(1-methylpropyl) sulfosuccinate, di(n-pentyl) sulfosuccinate, di(1-methylbutyl) sulfosuccinate, di(2-methylbutyl) sulfosuccinate, di(isoamyl) sulfosuccinate, di(2,2-dimethylpropyl)) sulfosuccinate, di(n-hexyl) sulfosuccinate, di(2-ethylbutyl) sulfosuccinate, di(cyclohexyl) sulfosuccinate, di(3-methylpentyl) sulfosuccinate, di(1-methylpentyl) sulfosuccinate, di(n-heptyl) sulfosuccinate, di(5-methylhexyl) sulfosuccinate, di(1-methylhexyl) sulfosuccinate, di(2-ethylpentyl) sulfosuccinate, di (1,3-dimethylbutyl)sulfosuccinate, diamyl sulfosuccinate, diisobutyl sulfosuccinate, or a combination thereof.

Embodiment 6

The surfactant system according to embodiment 5, wherein the second diester sulfosuccinate surfactant compound according to formula (II) is sodium di (1,3-dimethylbutyl) sulfosuccinate, sodium diamyl sulfosuccinate, sodium diisobutyl sulfosuccinate, or a combination thereof.

Embodiment 7

The surfactant system according to any one of the preceding embodiments, wherein the first diester sulfosuccinate surfactant is present in the surfactant system in a weight % ratio from 45 wt. % to 80 wt. % based on the total weight of the surfactant system, and the second diester sulfosuccinate surfactant is present in the surfactant system in a weight % ratio from 20 wt. % to 55 wt. % based on the total weight of the surfactant system.

Embodiment 8

A surfactant system comprising:
a mixture of:
(a) one or more of a first diester sulfosuccinate surfactant compound according to formula (I):

$$R^1\text{—O—CO—CHX—CHY—CO—O—}R^2 \qquad (I)$$

wherein:
$R^1$ and $R^2$ are linear or branched alkyl groups, each independently having from eight to thirteen carbon atoms,
X is —H or —$SO_3^-M^+$, and
Y is —H or —$SO_3^-M^+$.
when X is —H, then Y is —$SO_3^-M^+$ and when Y is —H, then X is —$SO_3^-M^+$, where $M^+$ is $H^+$, $Na^+$, $Ca^+$, $Mg^+$, $K^+$, $NH_4^+$, $NR_4^+$, where R is H, methyl, ethyl, propyl or butyl; and
(b) one or more of a first monoester sulfosuccinate surfactant compound according to formula (III):

$$B^+\text{—O—CO—CHX—CHY—CO—O}(CH2\text{-}CH2\text{-}O)_z\text{—}R^5 \qquad (III)$$

wherein:
$B^+$ is $Na^+$, $K^+$, $Ca^+$, $Mg^+$, $NH4^+$, or $NR4^+$, where R is H, methyl, ethyl, propyl or butyl,
X is as defined for formula (I),
Y is as defined for formula (I), and
Z is 0-30, and
$R^5$ is a linear or branched alkyl group having from eight to twenty carbon atoms (C8-C20).

Embodiment 9

The surfactant system according to embodiment 8, wherein the first diester sulfosuccinate surfactant compound is present in the surfactant system in a weight % ratio from 45 wt. % to 80 wt. % based on the total weight of the surfactant system, and the first monoester sulfosuccinate surfactant compound is present in the surfactant system in a weight % ratio from 20 wt. % to 55 wt. % based on the total weight of the surfactant system.

Embodiment 10

The surfactant system according to one of embodiments 8 and 9, wherein the first diester sulfosuccinate surfactant compound is sodium bistridecyl sulfosuccinate or sodium di(2-ethyl hexyl) sulfosuccinate.

Embodiment 11

The surfactant system according to embodiment 8, wherein $B^+$ is $Na^+$.

Embodiment 12

The surfactant system according to any one of embodiments 8-11, wherein the first monoester sulfosuccinate surfactant compound is:
(a) disodium salt of poly(oxy-1,2-ethanediyl),α-(3-carboxy-1-oxosulfopropyl)-ω-hydroxy-C10-C16-alykyl ethers;
(b) disodium salts of butanedioic acid, 2-sulfo-,C9-11 isoalkyl esters, C10-rich; disodium salts of poly(oxy-1,2-ethanediyl),α-(3-carboxy-1-oxosulfopropyl)-ω-hydroxy-C12-14-alkyl ethers; and disodium salts of poly(oxy-1,2-ethanediyl),α-(3-carboxy-1-oxosulfopropyl)-ω-hydroxy-C10-12-alkyl ethers; or
(c) sodium salt of poly(oxy-1,2-ethanediyl),α-(3-carboxy-1-oxosulfopropyl)-ω-(isotridecyloxy).

Embodiment 13

The surfactant system according to any one of embodiments 8-12, further comprising a second diester sulfosuccinate surfactant compound according to formula (II):

$$R^3\text{—O—CO—CHX—CHY—CO—O—}R^4 \qquad (II)$$

wherein:
$R^3$ and $R^4$ are linear or branched alkyl groups, each independently having from four to seven carbon atoms,
X is as defined according to formula (I), and
Y is as defined according to formula (I).

Embodiment 14

The surfactant system according to embodiment 13, wherein the first diester sulfosuccinate surfactant compound is present in the surfactant system in a weight % ratio from 50 wt. % to 65 wt. % based on the total weight of the surfactant system, the second diester sulfosuccinate surfactant compound is present in the surfactant system in a weight % ratio from 20 wt. % to 30 wt. % based on the total weight of the surfactant system, and the first monoester sulfosuccinate surfactant compound is present in the surfactant system in a weight % ratio from 10 wt. % to 20 wt. % based on the total weight of the surfactant system.

Embodiment 15

The surfactant system according to any one of embodiments 13-14, wherein the second diester sulfosuccinate surfactant compound according to formula (II) is a salt of di(n-butyl) sulfosuccinate, di(t-butyl) sulfosuccinate, di(1-methylpropyl) sulfosuccinate, di(n-pentyl) sulfosuccinate, di(1-methylbutyl) sulfosuccinate, di(2-methylbutyl) sulfosuccinate, di(isoamyl) sulfosuccinate, di(2,2-dimethylpropyl)) sulfosuccinate, di(n-hexyl) sulfosuccinate, di(2-ethylbutyl) sulfosuccinate, di(cyclohexyl) sulfosuccinate, di(3-methylpentyl) sulfosuccinate, di(1-methylpentyl) sulfosuccinate, di(n-heptyl) sulfosuccinate, di(5-methylhexyl) sulfo- The experiments were conducted over a range of temperatures from 25 to 60° C. Table 1 provides the compounds utilized in the tested surfactant systems.

TABLE 1

| Surfactant Tradename | CAS Number | Chemical Name | Generic Chemical Class |
|---|---|---|---|
| AEROSOL TR | 848588-96-5 | Sodium bistridecyl sulfosuccinate | Diester Sulfosuccinate |
| AEROSOL OT | 577-11-7 | Sodium di(2-ethylhexyl) sulfosuccinate* | Diester Sulfosuccinate |
| AEROSOL MA | 2373-38-8 | Sodium di (1,3-Dimethylbutyl) Sulfosuccinate | Diester Sulfosuccinate |
| AEROSOL AY | 922-90-5 | Sodium diamyl sulfosuccinate | Diester Sulfosuccinate |
| AEROSOL IB | 127-39-9 | Sodium diisobutyl sulfosuccinate | Diester Sulfosuccinate |
| AEROSOL A-102 | 68815-56-5 | Poly(oxy-1,2-ethanediyl), α-(3-carboxy-1-oxo sulfopropyl)-ω-hydroxy-, C10-16-alkyl ethers, disodium salts | Monoester Sulfosuccinate |
| AEROSOL EF-800 | 815583-9-6 | Butanedioic acid, 2-sulfo-, C9-11-isoalkyl esters, C10-rich, disodium salts | Monoester Sulfosuccinate |
| | 1024612-24-5 | Poly(oxy-1,2-ethanediyl), α-(3-carboxy-1-oxosulfopropyl)-ω-hydroxy-, C12-14-alkyl ethers, disodium salts | |
| | 68954-91-6 | Poly(oxy-1,2-ethanediyl), α-(3-carboxy-1-oxosulfopropyl)-ω-hydroxy-, C10-12-alkyl ethers, disodium salts | |
| AEROSOL EF-810 | 1013906-64-3 | Poly(oxy-1,2-ethanediyl), α-(3-carboxy-1-oxosulfopropyl)-ω-(isotridecyloxy)-, sodium salt (1:2) | Monoester Sulfosuccinate |

*Also commonly referred to as sodium dioctyl sulfosuccinate succinate, di(1-methylhexyl) sulfosuccinate, di(2-ethylpentyl) sulfosuccinate, di (1,3-dimethylbutyl) sulfosuccinate, diamyl sulfosuccinate, diisobutyl sulfosuccinate, or a combination thereof.

Embodiment 16

The surfactant system according to any one of embodiments 13-15, wherein the second diester sulfosuccinate surfactant compound according to formula (II) is sodium di (1,3-dimethylbutyl) sulfosuccinate, sodium diamyl sulfosuccinate, sodium diisobutyl sulfosuccinate or a combination thereof.

Embodiment 17

A method of using the surfactant system according to any one of the preceding embodiments in recovery of oil from a subterranean formation, the method comprising:
combining an effective amount of the surfactant system according to any one of the preceding embodiments with a brine to form a solution;
injecting an effective amount of the solution into a subterranean formation; and
increasing a pressure in the subterranean formation, thereby enabling the recovery of oil from the subterranean formation.

Examples

The following examples are included herein to provide information on certain aspects of the invention and are not meant to limit the invention to the exemplified formulations.

The surfactant systems were incorporated at a 0.5% concentration into water and NaCl/CaCl$_2$ brines ranging from 1.05 to 12.05% in salinity. The brines were principally comprised of 1.0 to 12.0% NaCl, and additionally contained 0.05% CaCl$_2$. For the majority of the work, the brine solution was 3.05%. For the high salinity brines, the range was 7.05 to 12.05%. The oil used in the examples was dodecane.

AEROSOL TR, AEROSOL OT, AEROSOL MA, AEROSOL AY and AEROSOL IB are commercially available from Cytec Solvay as AEROSOL TR-70, AEROSOL OT-70PG, AEROSOL MA-80PG, AEROSOL AY-65 and AEROSOL IB-45, respectively.

The 3.05% brine solution was prepared by dissolving 3% sodium chloride (Crystal ACS grade, Lot-0000130743, Marcon Fine Chemicals) and 0.05% calcium chloride (Anhydrous 96% Pure, Lot-A0253415, Acros Organics) into deionized (DI) water. In select experiments, DI water alone served as the base solution.

The test solutions were prepared by charging the brine to a flask and adding 0.5% by weight of the surfactant system and the solution mixed for 60 minutes to ensure the preparation of a homogeneous solution. The experiments were conducted with the surfactant system incorporated into the aqueous solution at a 0.5% active weight concentration as noted above. For example—for 80% wt. surfactant system 0.5×100/80=0.625 grams added into 100 grams solution.

Surface tension measurements were taken on a Kruss K-12 Tensiometer.

Interfacial tension measurements were performed by a spinning drop technique by injecting a drop of oil into the surfactant system. The oil utilized in this experiment was a 100% dodecane (99% anhydrous, Lot-65796EM, Sigma Aldrich). Interfacial tension measurements were conducted on a Kruss Site 100 Spinning Drop Tensiometer.

The visual appearance of each solution was noted. Solutions were categorized as Clear, Clear to Hazy, or Hazy. Turbidity measurements were made on an HACH 2100 Turbidimeter.

The following tables exemplify the performances of the individual surfactant compounds and the surfactant systems that combine two or more of the individual surfactant compounds.

All of the surfactant systems were evaluated at a total concentration of 0.5% weight percent in the aqueous DI water and 3.05% brine solutions. For each surfactant compound and surfactant system, the surface and interfacial tension is reported.

The examples illustrate the inventors' surprising discovery that by combining diester sulfosuccinate and mono and diester sulfosuccinate surfactant compounds, one is able to achieve a synergistic performance that provides reduced or similar surface tension as compared to individual surfactant compounds and also provides greatly reduced interfacial tensions. It is also noted that in some systems, the incorporation of the third component, a monoester sulfosuccinate surfactant compound, can further enhance the performance of the formulation. Surfactant systems having the third component have even further reduced interfacial tension and improved turbidity, as solutions are less hazy indicating an increased compatibility of the formulation in the brine solution.

Examples are also presented on the performance of these novel formulations over a range of salinities and temperatures.

Table 2 below exemplifies some of the lead systems and their performance in a 3.05% brine solution in a dodecane oil mixture.

TABLE 2

Surface Tension, Interfacial Tension, Appearance and Turbidity in 3.05% brine

| Surfactant | % Ratio (Weight) | Wt % (Conc.) | Surface Tension, mN/m | Interfacial Tension, mN/m (Dodecane) | Appearance, Visual | Turbidity, NTU |
|---|---|---|---|---|---|---|
| AEROSOL TR | 100 | 0.5 | Not Measured | Not Measured | Precipitation, white aggregates | Not Measured |
| AEROSOL OT | 100 | 0.5 | 25.5 | 0.586 | Clear Hazy Liquid | 614 |
| AEROSOL MA | 100 | 0.5 | 24.2 | 1.38 | Clear liquid | 1.4 |
| AEROSOL AY | 100 | 0.5 | 31.6 | 7.44 | Clear to slightly hazy Liquid | 11.4 |
| AEROSOL IB | 100 | 0.5 | 27.1 | 1.21 | Clear to slightly hazy Liquid | 14 |
| AEROSOL A-102 | 100 | 0.5 | 34.4 | 4.225 | Clear liquid | 0.7 |
| AEROSOL EF-800 | 100 | 0.5 | 30.1 | 4.96 | Clear liquid | 2 |
| AEROSOL EF-810 | 100 | 0.5 | 33.1 | 4.64 | Clear liquid | 0.7 |
| AEROSOL TR-AEROSOL IB | 62-38 | 0.5 | Not Measured | Not Measured | Precipitation, white aggregates | Not Measured |
| AEROSOL TR-AEROSOL AY | 55-45 | 0.5 | 25.7 | 1.32 | Precipitation- 5 minutes | 218 |
| AEROSOL TR-AEROSOL MA | 48-52 | 0.5 | 25.6 | 0.727 | Hazy liquid | 500 |
| AEROSOL TR-AEROSOL A-102 | 48-52 | 0.5 | 26.6 | 0.057 | Hazy liquid | 1000 |
| AEROSOL TR-AEROSOL EF-800 | 69-31 | 0.5 | 25.7 | 1.61 | Hazy liquid | 1000 |
| AEROSOL TR-AEROSOL EF-810 | 48-52 | 0.5 | 26.9 | 0.071 | Hazy liquid | 1000 |
| AEROSOL OT-AEROSOL IB | 70-30 | 0.5 | 25.3 | 0.556 | Precipitation, white aggregates | 235 |
| AEROSOL OT-AEROSOL AY | 64-36 | 0.5 | 25.1 | 0.225 | Hazy liquid | 414 |
| AEROSOL OT-AEROSOL MA | 56-44 | 0.5 | 25.8 | 0.084 | Hazy liquid | 194 |
| AEROSOL OT-AEROSOL A-102 | 57-43 | 0.5 | 25.7 | 0.122 | Hazy liquid | 271 |
| AEROSOL OT-AEROSOL EF-800 | 76-24 | 0.5 | 25.3 | 0.181 | Hazy liquid | 308 |
| AEROSOL OT-AEROSOL EF-810 | 57-43 | 0.5 | 25.9 | 0.102 | Hazy liquid | 656 |
| AEROSOL OT-AEROSOL MA-AEROSOL A-102 | 56-24-20 | 0.5 | 25.3 | 0.008 | Hazy Liquid | 776 |
| AEROSOL OT-AEROSOL MA-AEROSOL EF-800 | 64-26-10 | 0.5 | 25 | 0.114 | Hazy Liquid | 213 |
| AEROSOL OT-AEROSOL MA-AEROSOL EF-810 | 56-24-20 | 0.5 | 25.4 | 0.007 | Hazy Liquid | 904 |

Many surfactant compounds cannot lower surface and interfacial tension in high salinity environments (i.e. 6.05 to 12.05% salinity). Many times, at high salinity, the high concentration of ions renders the surfactant compounds ineffective, or causes active precipitation of the surfactant compounds. Table 3 below exemplifies how systems according to the present invention that include monoester sulfosuccinate surfactant compounds and diester sulfosuccinate surfactant compounds, when combined, yield synergistic surfactant systems that exhibit unexpected superior performance by lowering surface and interfacial tension in high salinity 8.05% brine.

TABLE 3

Surface Tension, Interfacial Tension, Appearance and Turbidity in 8.05% brine

| Surfactant | % Ratio (Weight) | Wt % (Conc) | Surface Tension, mN/m | Interfacial Tension, mN/m (Dodecane) | Appearance, Visual | Turbidity, NTU |
|---|---|---|---|---|---|---|
| AEROSOL OT | 100 | 0.5 | 25.5 | 1.42 | Hazy Liquid | 1000 |
| AEROSOL A-102 | 100 | 0.5 | 32.6 | 3.42 | Clear Liquid | 0.81 |
| AEROSOL EF-800 | 100 | 0.5 | 29.3 | 4.63 | Clear Liquid | 1.1 |
| AEROSOL EF-810 | 100 | 0.5 | 32.0 | 3.01 | Clear Liquid | 5.2 |
| AEROSOL OT-AEROSOL A-102 | 36-64 | 0.5 | 26.1 | 0.214 | Hazy Liquid | 1000 |
| AEROSOL OT-AEROSOL EF-800 | 62-38 | 0.5 | 25.2 | 0.1 | Hazy Liquid | 431 |
| AEROSOL OT-AEROSOL EF-810 | 38-62 | 0.5 | 26.2 | 0.137 | Hazy Liquid | 1000 |

As illustrated in Table 4 below, combinations of monoester sulfosuccinate surfactant compounds and diester sulfosuccinate surfactant compounds, when combined as ternary surfactant system, yield synergistic systems that exhibit unexpected superior performance, and lower surface and interfacial tension in brine solutions ranging from 3.05 to 12.05% salinity. Ternary surfactant systems are compatible in high brine solutions.

TABLE 4

Surface Tension, Interfacial Tension, Appearance and Turbidity in brines of varying salinity

| Surfactant | % Ratio (Wt) | Wt % (Conc) | Salinity | Surface Tension mN/m | Interfacial Tension, mN/m (Dodecane) | Appear, Visual | Turbidity NTU |
|---|---|---|---|---|---|---|---|
| AEROSOL OT-AEROSOL MA | 56-44 | 0.5 | 3.05 | 24.8 | 0.093 | Hazy Liquid | 194 |
| AEROSOL OT-AEROSOL MA | 56-44 | 0.5 | 6.05 | 24.7 | 0.293 | Hazy Liquid | 1000 |
| AEROSOL OT-AEROSOL MA-AEROSOL A-102 | 56-24-20 | 0.5 | 3.05 | 25.3 | 0.008 | Hazy Liquid | 776 |
| AEROSOL OT-AEROSOL MA-AEROSOL A-102 | 56-24-20 | 0.5 | 6.05 | 24.9 | 0.06 | Hazy Liquid | 239 |
| AEROSOL OT-AEROSOL MA-AEROSOL A-102 | 56-24-20 | 0.5 | 7.05 | 24.9 | 0.109 | Hazy Liquid | 609 |
| AEROSOL OT-AEROSOL MA-AEROSOL A-102 | 56-24-20 | 0.5 | 8.05 | 24.9 | 0.152 | Hazy Liquid | 1000 |
| AEROSOL OT-AEROSOL MA-AEROSOL A-102 | 56-24-20 | 0.5 | 9.05 | 24.8 | 0.217 | Hazy Liquid | 1000 |
| AEROSOL OT-AEROSOL MA-AEROSOL A-102 | 56-24-20 | 0.5 | 10.05 | 24.8 | 0.253 | Hazy Liquid | 1000 |

TABLE 4-continued

Surface Tension, Interfacial Tension, Appearance and Turbidity in brines of varying salinity

| Surfactant | % Ratio (Wt) | Wt % (Conc) | Salinity | Surface Tension mN/m | Interfacial Tension, mN/m (Dodecane) | Appear, Visual | Turbidity NTU |
|---|---|---|---|---|---|---|---|
| AEROSOL OT-AEROSOL MA-AEROSOL A-102 | 56-24-20 | 0.5 | 11.05 | 24.7 | 0.264 | Hazy Liquid | 1000 |
| AEROSOL OT-AEROSOL MA-AEROSOL A-102 | 56-24-20 | 0.5 | 12.05 | 24.6 | 0.37 | Hazy Liquid | 1000 |

In subterranean formations, temperatures may vary broadly and this can greatly impact surfactant performance. Accordingly, it is highly advantageous if a surfactant system can demonstrate functionality over a broad range of temperatures. The data in Tables 5A and 5B demonstrate the performance of binary and ternary surfactant systems according to the present invention in lowering surface and interfacial tensions over a broad temperature range across varying salinities.

TABLE 5A

Surface Tension, Interfacial Tension, Appearance and Turbidity in 3.05% Brine at Varying Temperatures

| Surfactant | % Ratio (Weight) | Wt % (Conc.) | Temp (° C.) | Surface Tension, mN/m | Interfacial Tension, mN/m (Dodecane) | Appearance, Visual | Turbidity, NTU |
|---|---|---|---|---|---|---|---|
| AEROSOL OT-AEROSOL MA | 56-44 | 0.5 | 25 | 24.8 | 0.084 | Hazy liquid | 194 |
| AEROSOL OT-AEROSOL MA | 56-44 | 0.5 | 30 | 24.3 | 0.094 | Hazy liquid | Not Measured |
| AEROSOL OT-AEROSOL MA | 56-44 | 0.5 | 40 | 23.8 | 0.093 | Hazy liquid | Not Measured |
| AEROSOL OT-AEROSOL MA | 56-44 | 0.5 | 50 | 23.4 | 0.089 | Hazy liquid | Not Measured |
| AEROSOL OT-AEROSOL MA | 56-44 | 0.5 | 60 | 24.9 | 0.072 | Hazy liquid | Not Measured |

TABLE 5B

Surface Tension, Interfacial Tension, Appearance and Turbidity in 8.05% Brine at Varying Temperatures

| Surfactant | % Ratio (Weight) | Wt % (Conc.) | Temp (° C.) | Surface Tension, mN/m | Interfacial Tension, mN/m (Dodecane) | Appear | Turbidity, NTU |
|---|---|---|---|---|---|---|---|
| AEROSOL OT-AEROSOL EF-800 | 62-38 | 0.5 | 25 | 25.2 | 0.100 | Hazy liquid | 431 |
| AEROSOL OT-AEROSOL EF-800 | 62-38 | 0.5 | 30 | 24.8 | 0.098 | Hazy liquid | Not Measured |
| AEROSOL OT-AEROSOL EF-800 | 62-38 | 0.5 | 40 | 24.2 | 0.092 | Hazy liquid | Not Measured |
| AEROSOL OT-AEROSOL EF-800 | 62-38 | 0.5 | 50 | 23.8 | 0.080 | Hazy liquid | Not Measured |
| AEROSOL OT-AEROSOL EF-800 | 62-38 | 0.5 | 60 | 23.4 | 0.093 | Hazy liquid | Not Measured |
| AEROSOL OT-AEROSOL MA-AEROSOL A-102 | 56-24-20 | 0.5 | 25 | 24.8 | 0.152 | Hazy liquid | 1000 |
| AEROSOL OT-AEROSOL MA-AEROSOL A-102 | 56-24-20 | 0.5 | 30 | 24.7 | 0.14 | Hazy liquid | Not Measured |
| AEROSOL OT-AEROSOL MA-AEROSOL A-102 | 56-24-20 | 0.5 | 40 | 24.2 | 0.14 | Hazy liquid | Not Measured |

TABLE 5B-continued

Surface Tension, Interfacial Tension, Appearance
and Turbidity in 8.05% Brine at Varying Temperatures

| Surfactant | % Ratio (Weight) | Wt % (Conc.) | Temp (° C.) | Surface Tension, mN/m | Interfacial Tension, mN/m (Dodecane) | Appear | Turbidity, NTU |
|---|---|---|---|---|---|---|---|
| AEROSOL OT-AEROSOL MA-AEROSOL A-102 | 56-24-20 | 0.5 | 50 | 24.1 | 0.136 | Hazy liquid | Not Measured |
| AEROSOL OT-AEROSOL MA-AEROSOL A-102 | 56-24-20 | 0.5 | 60 | 23.9 | 0.136 | Hazy liquid | Not Measured |

Tables 6A and 6B below exemplifies how select binary surfactant systems according to the present invention continue to evidence synergy and offer both low surface and interfacial tension at 3.05 and 8.05% salinities across a range of weight ratios of approximately 25/75, 50/50 and 75/25.

TABLE 6A

Surface Tension, Interfacial Tension, Appearance
and Turbidity in 3.05% Brine

| Surfactant | % Ratio (Weight) | Wt % (Conc.) | Surface Tension, mN/m | Interfacial Tension, mN/m (Dodecane) | Appearance, Visual | Turbidity, NTU |
|---|---|---|---|---|---|---|
| AEROSOL OT | 100 | 0.5 | 25.5 | 0.586 | Clear Hazy Liquid | 614 |
| AEROSOL MA | 100 | 0.5 | 24.2 | 1.38 | Clear liquid | 1.4 |
| AEROSOL A-102 | 100 | 0.5 | 34.4 | 4.225 | Clear liquid | 0.7 |
| AEROSOL OT-AEROSOL MA | 24-76 | 0.5 | 24.6 | 0.114 | Hazy liquid | 92 |
| AEROSOL OT-AEROSOL MA | 56-44 | 0.5 | 25.8 | 0.084 | Hazy liquid | 194 |
| AEROSOL OT-AEROSOL MA | 75-25 | 0.5 | 25.6 | 0.214 | Hazy liquid | 808 |
| AEROSOL OT-AEROSOL A-102 | | 0.5 | 26 | 0.493 | Hazy liquid | 2.8 |
| AEROSOL OT-AEROSOL A-102 | 57-43 | 0.5 | 25.7 | 0.122 | Hazy liquid | 271 |
| AEROSOL OT-AEROSOL A-102 | 75-25 | 0.5 | 25.6 | 0.035 | Hazy liquid | 808 |

TABLE 6B

Surface Tension, Interfacial Tension, Appearance
and Turbidity in 8.05% Brine

| Surfactant | % Ratio (Weight) | Wt % | Surface Tension, mN/m | Interfacial Tension, mN/m (Dodecane) | Appearance, Visual | Turbidity, NTU |
|---|---|---|---|---|---|---|
| AEROSOL OT | 100 | 0.5 | 25.5 | 1.42 | Hazy Liquid | 1000 |
| AEROSOL EF-800 | 100 | 0.5 | 29.3 | 4.63 | Clear Liquid | 1.1 |
| AEROSOL OT-AEROSOL EF-800 | 25-75 | 0.5 | 25.3 | 0.444 | Hazy Liquid | 237 |
| AEROSOL OT-AEROSOL EF-800 | 62-38 | 0.5 | 25.2 | 0.100 | Hazy Liquid | 431 |
| AEROSOL OT-AEROSOL EF-800 | 75-25 | 0.5 | 25.2 | 0.377 | Hazy Liquid | 379 |

As used herein, the terms "a" and "an" do not denote a limitation of quantity, but rather the presence of at least one of the referenced items. Recitation of ranges of values are merely intended to serve as a shorthand method of referring individually to each separate value falling within the range, and each separate value is incorporated into this specification as if it were individually recited. Thus, each range disclosed herein constitutes a disclosure of any sub-range falling within the disclosed range. Disclosure of a narrower range or more specific group in addition to a broader range or larger group is not a disclaimer of the broader range or larger group.

All ranges disclosed herein are inclusive of the endpoints, and the endpoints are independently combinable with each other. "Comprises" as used herein includes embodiments "consisting essentially of" or "consisting of" the listed elements.

Although the foregoing description has shown, described, and pointed out the fundamental novel features of certain embodiments of the present invention, it will be understood that various omissions, substitutions, and changes in the form of the detail of the invention as described may be made by those skilled in the art, without departing from the spirit and scope of the present teachings. Consequently, the scope of the present invention should not be limited to the foregoing examples, description or discussion.

What is claimed is:

1. An oil recovery surfactant system comprising:
a mixture of:
(a) one or more of a first diester sulfosuccinate surfactant compound according to formula (I):

$$R^1-O-CO-CHX-CHY-CO-O-R^2 \quad (I)$$

wherein:
R$^1$ and R$^2$ are linear or branched alkyl groups, each independently having from eight to thirteen carbon atoms,
X is —H or —SO$_3^-$M$^+$, and
Y is —H or —SO$_3^-$M$^+$,
when X is —H, then Y is —SO$_3^-$M$^+$ and when Y is —H, then X is —SO$_3^-$M$^+$, where M$^+$ is H$^+$, Na$^+$, Ca$^+$, Mg$^+$, K$^+$, NH$_4^+$, NR$_4^+$, where R is H, methyl, ethyl, propyl or butyl; and
(b) one or more of a first monoester sulfosuccinate surfactant compound according to formula (III):

$$B^+-O-CO-CHX-CHY-CO-O(CH2\text{-}CH2\text{-}O)_z-R^5 \quad (III)$$

wherein:
B$^+$ is Na$^+$, K$^+$, Ca$^+$, Mg$^+$, NH$_4^+$, or NR$_4^+$, where R is H, methyl, ethyl, propyl or butyl,
X is as defined for formula (I),
Y is as defined for formula (I), and
Z is 0-30, and
R$^5$ is a linear or branched alkyl group having from eight to twenty carbon atoms (C8-C20),
wherein the first diester sulfosuccinate surfactant compound is present in the surfactant system in a weight % ratio from 45 wt. % to 80 wt. % based on the total weight of the surfactant system, and the first monoester sulfosuccinate surfactant compound is present in the surfactant system in a weight % ratio from 20 wt. % to 55 wt. % based on the total weight of the surfactant system.

2. The oil recovery surfactant system according to claim 1, wherein the first diester sulfosuccinate surfactant compound is sodium bistridecyl sulfosuccinate or sodium di(2-ethyl hexyl) sulfosuccinate.

3. The oil recovery surfactant system according to claim 1, wherein B$^+$ is Na$^+$.

4. The oil recovery surfactant system according to claim 3, wherein the first monoester sulfosuccinate surfactant compound is:
(a) disodium salt of poly(oxy-1,2-ethanediyl), α-(3-carboxy-1-oxosulfopropyl)-ω-hydroxy-C10-C16-alkyl ethers;
(b) disodium salts of butanedioic acid, 2-sulfo-,C9-11 isoalkyl esters, C10-rich; disodium salts of poly(oxy-1,2-ethanediyl), α-(3-carboxy-1-oxosulfopropyl)-ω-hydroxy-C12-14-alkyl ethers; and disodium salts of poly(oxy-1,2-ethanediyl), α-(3-carboxy-1-oxosulfopropyl)-ω-hydroxy-C10-12-alkyl ethers; or
(c) sodium salt of poly(oxy-1,2-ethanediyl), α-(3-carboxy-1-oxosulfopropyl)-ω-(isotridecyloxy).

5. The oil recovery surfactant system according to claim 1, further comprising a second diester sulfosuccinate surfactant compound according to formula (II):

$$R^3-O-CO-CHX-CHY-CO-O-R^4 \quad (II)$$

wherein:
R$^3$ and R$^4$ are linear or branched alkyl groups, each independently having from four to seven carbon atoms,
X is as defined according to formula (I), and
Y is as defined according to formula (I).

6. The oil recovery surfactant system according to claim 5, wherein the first diester sulfosuccinate surfactant compound is present in the surfactant system in a weight % ratio from 50 wt. % to 65 wt. % based on the total weight of the surfactant system, the second diester sulfosuccinate surfactant compound is present in the surfactant system in a weight % ratio from 20 wt. % to 30 wt. % based on the total weight of the surfactant system, and the first monoester sulfosuccinate surfactant compound is present in the surfactant system in a weight % ratio from 10 wt. % to 20 wt. % based on the total weight of the surfactant system.

7. The oil recovery surfactant system according to claim 5, wherein the second diester sulfosuccinate surfactant compound according to formula (II) is a salt of di(n-butyl) sulfosuccinate, di(t-butyl) sulfosuccinate, di(1-methylpropyl) sulfosuccinate, di(n-pentyl) sulfosuccinate, di(1-methylbutyl) sulfosuccinate, di(2-methylbutyl) sulfosuccinate, di(isoamyl) sulfosuccinate, di(2,2-dimethylpropyl)) sulfosuccinate, di(n-hexyl) sulfosuccinate, di(2-ethylbutyl) sulfosuccinate, di(cyclohexyl) sulfosuccinate, di(3-methylpentyl) sulfosuccinate, di(1-methylpentyl) sulfosuccinate, di(n-heptyl) sulfosuccinate, di(5-methylhexyl) sulfosuccinate, di(1-methylhexyl) sulfosuccinate, di(2-ethylpentyl) sulfosuccinate, di (1,3-dimethylbutyl)sulfosuccinate, diamyl sulfosuccinate, diisobutyl sulfosuccinate, or a combination thereof.

8. The oil recovery surfactant system according to claim 7, wherein the second diester sulfosuccinate surfactant compound according to formula (II) is sodium di (1,3-dimethylbutyl) sulfosuccinate, sodium diamyl sulfosuccinate, sodium diisobutyl sulfosuccinate or a combination thereof.

9. A method of using the oil recovery surfactant system according to claim 1 in recovery of oil from a subterranean formation, the method comprising:
combining an effective amount of the oil recovery surfactant system according to claim 1 with a brine to form a solution;
injecting an effective amount of the solution into a subterranean formation; and
increasing a pressure in the subterranean formation, thereby enabling the recovery of oil from the subterranean formation.

* * * * *